(12) United States Patent
Su

(10) Patent No.: US 8,157,861 B2
(45) Date of Patent: Apr. 17, 2012

(54) REPLICA EYE

(75) Inventor: Xiao-Guang Su, Shenzhen (CN)

(73) Assignees: Hong Fu Jin Precision Industry (ShenZhen) Co., Ltd., Shenzhen, Guangdong Province (CN); Hon Hai Precision Industry Co., Ltd., Tu-Cheng, New Taipei (TW)

( * ) Notice: Subject to any disclaimer, the term of this patent is extended or adjusted under 35 U.S.C. 154(b) by 365 days.

(21) Appl. No.: 12/558,595

(22) Filed: Sep. 14, 2009

(65) Prior Publication Data

US 2010/0145443 A1 Jun. 10, 2010

(30) Foreign Application Priority Data

Dec. 5, 2008 (CN) .......................... 2008 1 0305996

(51) Int. Cl.
*A61F 2/16* (2006.01)
(52) U.S. Cl. ...................................... 623/6.64
(58) Field of Classification Search .................. 623/4.1, 623/6.64; 446/389
See application file for complete search history.

(56) References Cited

U.S. PATENT DOCUMENTS

| 4,272,910 A | * | 6/1981 | Danz .............................. 446/389 |
| 5,108,427 A | * | 4/1992 | Majercik et al. ............. 623/5.12 |
| 6,391,057 B1 | * | 5/2002 | Schleipman et al. ........ 623/6.64 |

* cited by examiner

Primary Examiner — William H. Matthews
(74) Attorney, Agent, or Firm — Altis Law Group, Inc.

(57) ABSTRACT

A replica eye includes an eyeball with a light-transmitting area for transmitting light, a resilient film, a driving member, and a transmission mechanism. The resilient film includes a pupil portion and an iris portion surrounding the pupil portion. The pupil portion is in a first color. The iris portion is in a second color other than the first color. The driving member has a shaft. The driving member provides rotating forces to the shaft. The transmission mechanism comprises a rotor fastened on the shaft of the driving member, and a plurality of flexible members in radial arrangement. A first end of each flexible member away from the rotor is fastened on an outer edge of the resilient film. When the driving member rotates the transmission mechanism, centrifugal forces are imparted on the plurality of flexible members, the plurality of flexible members stretches the pupil portion and the iris portion.

20 Claims, 5 Drawing Sheets

REPLICA EYE

BACKGROUND

1. Technical Field

The present disclosure relates to replicas of human organs, and particularly to a replica of an eye.

2. Description of Related Art

With the development of electronic technology, replica figures simulate the actions of living creatures, such as, walking, jumping, and others. Because eyes can be so expressive in living creatures, they have received much attention in the effort to allow replicas to simulate feelings.

However, most replicas of eyes only open and shut which is not very expressive. Therefore, what is needed are more expressive replica eyes.

DETAILED DESCRIPTION

Figure 1:
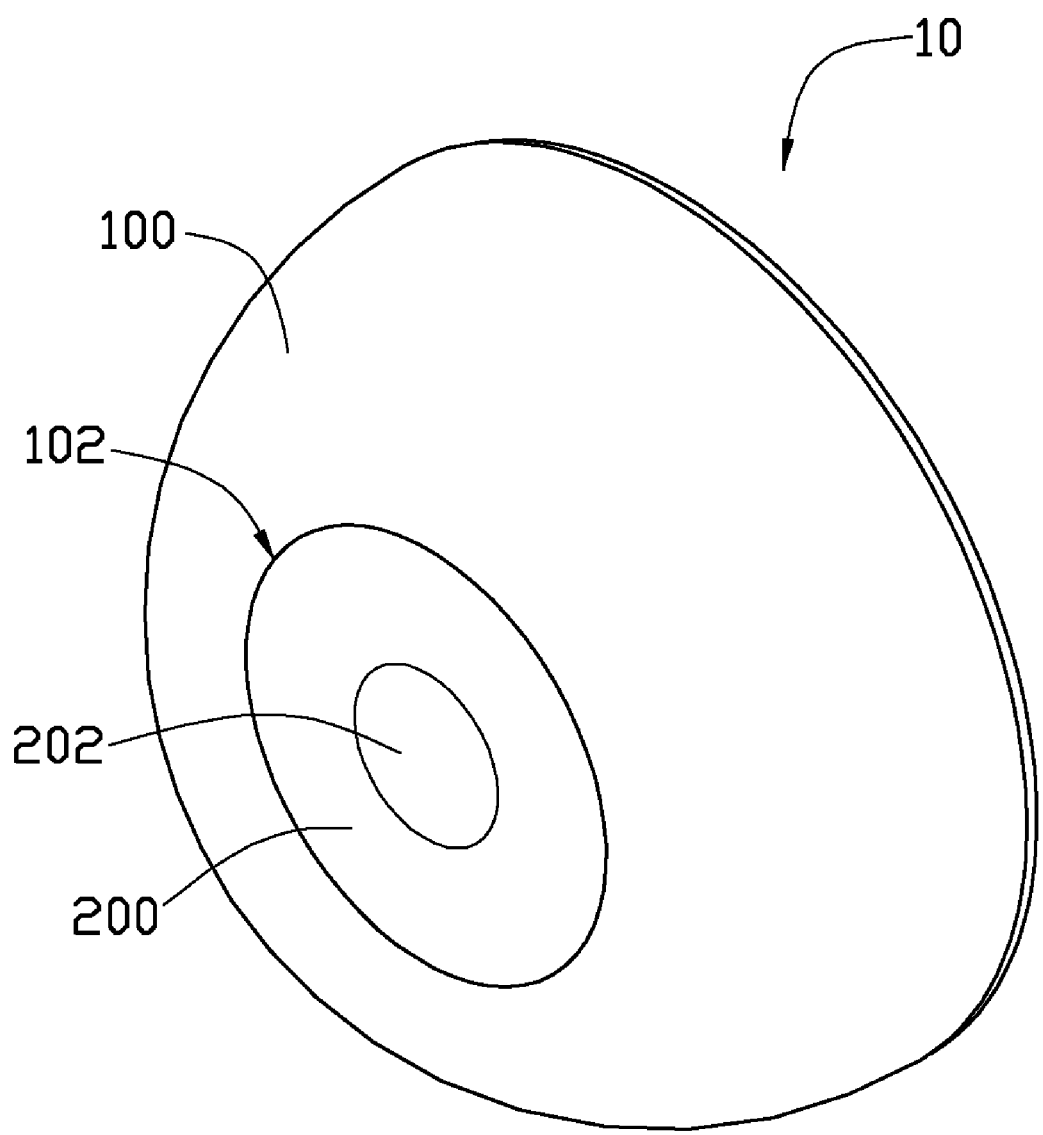
FIG. 1 is an isometric view of a replica eye in accordance with an exemplary embodiment.
Figure 2:
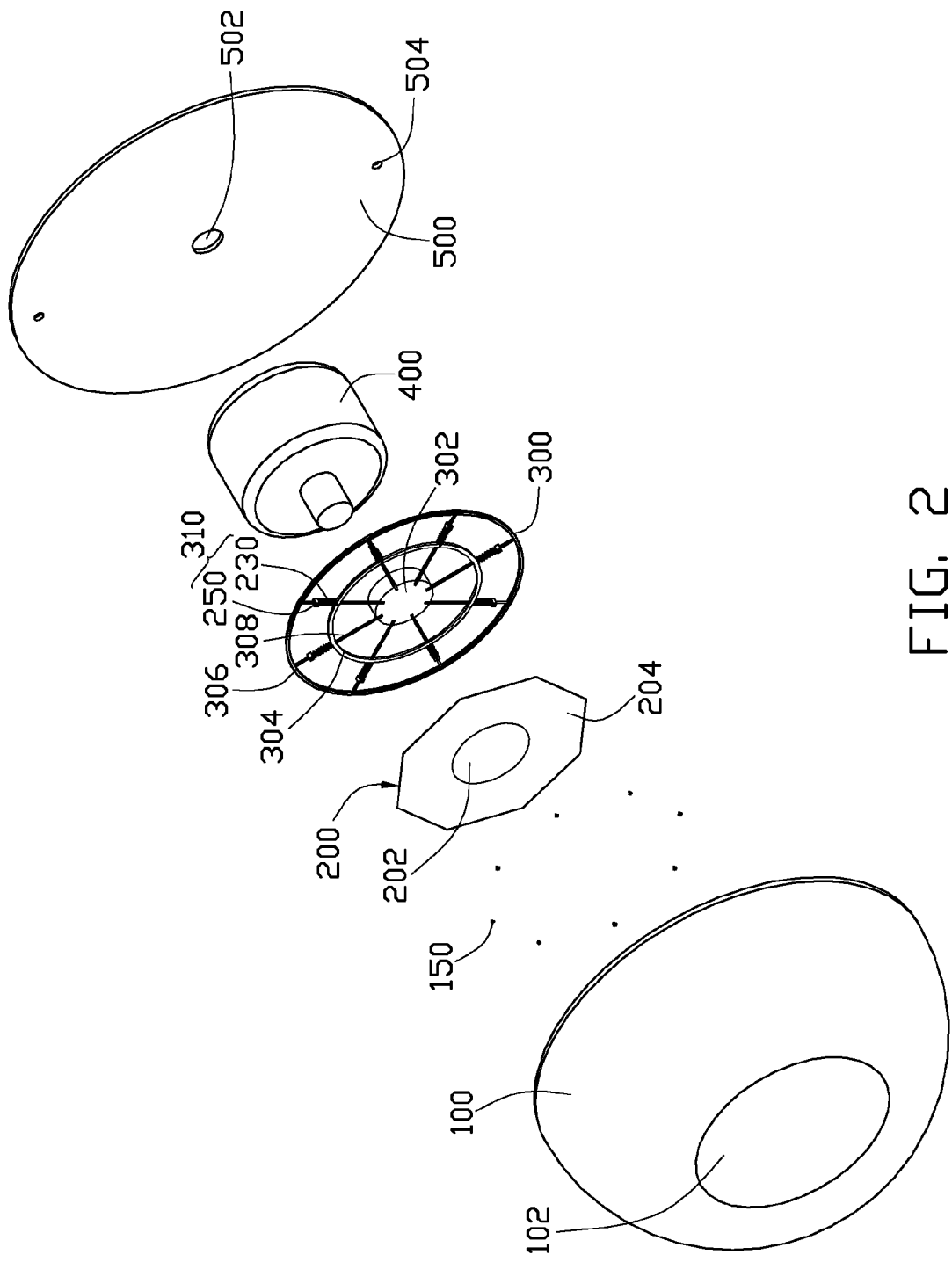
FIG. 2 is an exploded view of the replica eye of FIG. 1.

Referring to FIGS. 1 and 2, a replica eye 10 includes a hollow semi-spherical eyeball 100, a circular baseboard 500 fixed on back of the semi-spherical eyeball 100, a driving member 400 fixed on the baseboard 500, a transmission mechanism 300 fastened on the driving member 400, and a resilient film 200. The resilient film 200, the transmission mechanism 300, and the driving member 400 are received in the eyeball 100.

Figure 3:
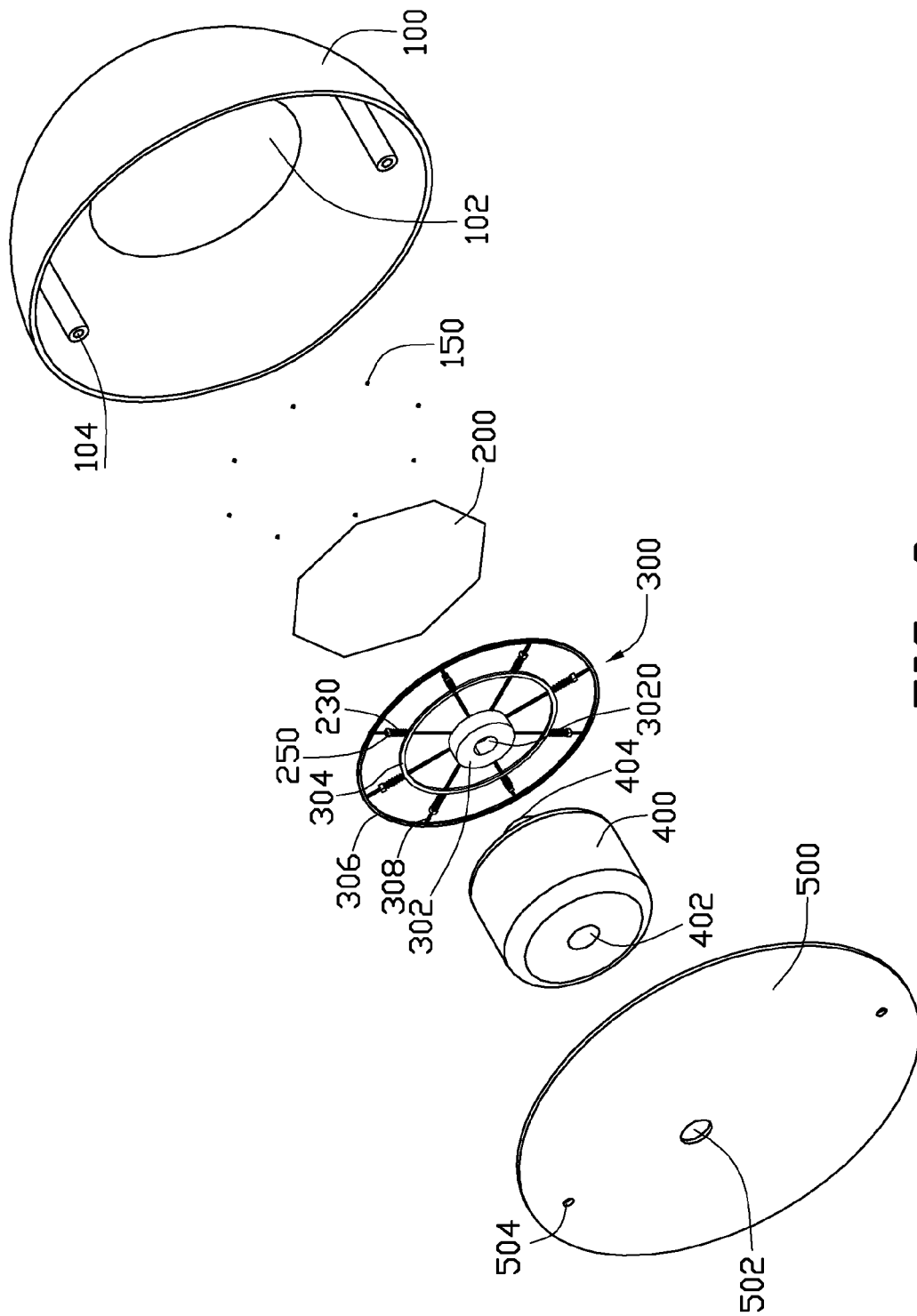
FIG. 3 is an exploded view of the replica eye of FIG. 1 from a reverse direction to FIG. 2.

Referring to FIGS. 2 and 3, the eyeball 100 has a circular transparent area 102 capable of transmitting light. The transparent area 102 is arranged on the front of the eyeball 100. In other embodiments, the eyeball 100 may define an opening in the front of the eyeball 100 instead of the transparent area 102. The eyeball 100 further includes two fixing posts 104. The fixing posts 104 may be threaded posts protruding from an inner surface of the eyeball 100.

The baseboard 500 defines a first through hole 502, and two second through holes 504. The first through hole 502 is defined in the center of the baseboard 500 and between the two second through holes 504.

The driving member 400 may be a cylindrical motor. The driving member 400 includes a shaft 404 protruding from one end thereof, and the transmission mechanism 300 is attached to the shaft 404. The driving member 400 also includes a fixing hole 402 such as a threaded hole defined in the other end away from the shaft 404. A fastener such as a screw (not shown) extends through the first through hole 502 and engages with the fixing hole 402 to fasten the driving member 400 to the baseboard 500. Two fasteners such as screws (not shown) after passing through the two second through holes 504 engage with the two fixing posts 104 correspondingly to fasten the eyeball 100 to the baseboard 500.

The resilient film 200 includes a circular pupil portion 202 and an iris portion 204 surrounding the pupil portion 202. The pupil portion 202 is a first color. The iris portion 204 is a second color other than the first color. In the embodiment, the resilient film 200 is octagonal. In other embodiments, the resilient film 200 may be some other polygonal shape such as triangular, quadrangular, pentagonal etc.

The transmission mechanism 300 includes a rotor 302, an inner wheel 304, an outer wheel 306, a plurality of spokes 308, a plurality of flexible members 310, and a plurality of screws 150. In particular, numbers of the spokes 308, the flexible members 310, and the screws 150 are arranged equal to the number of corners of the resilient film 200. In the embodiment, the numbers of the spokes 308, the flexible members 310 and the screws 150 are eight each.

The inner wheel 304 and the outer wheel 306 are concentric circles. The rotor 302 is arranged in the centers of the inner wheel 304 and the outer wheel 306. The rotor 302 defines a shaft hole 3020 for receiving the shaft 404 of the driving member 400. The shaft hole 3020 is arranged in the center of the rotor 302. The plurality of spokes 308 is in radial arrangement, and each spoke 308 extends from the rotor 302, passes through the inner wheel 304, and ends at the outer wheel 306.

The plurality of flexible members 310 is disposed between the inner wheel 304 and the outer wheel 306. Each flexible member 310 includes a heavy block 250 and a flexible component 230. Each flexible component 230 has a first end connected to the inner wheel 304, a second end opposite to the first end connected to the corresponding heavy block 250. The flexible components 230 and the heavy blocks 250 are sleeved on the corresponding spokes 308 and slidable with respect to the corresponding spokes 308. Each flexible component 230 may be a spring.

The plurality of screws 150 is used for fixing the corners of the resilient film 200 to the corresponding heavy block 250.

Figure 4:
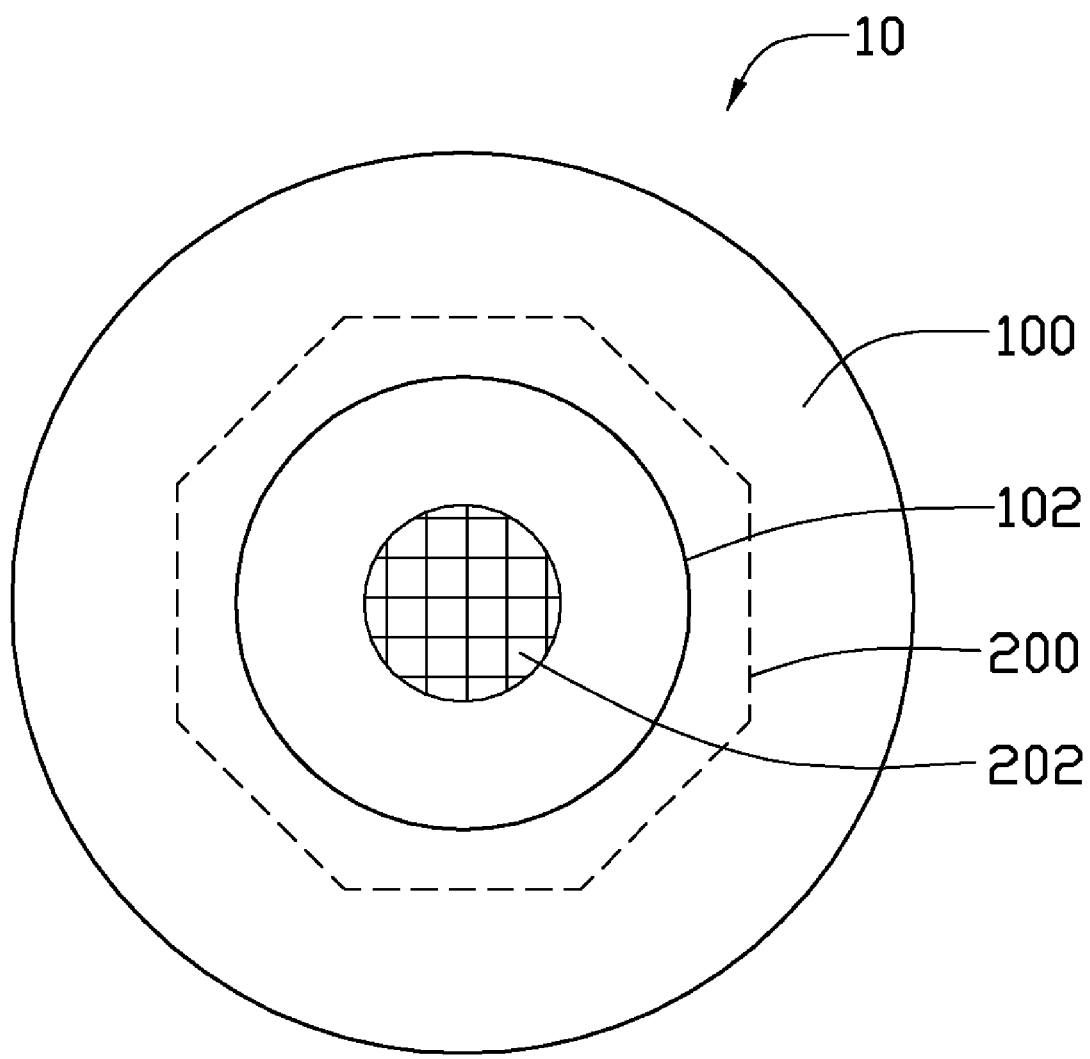
FIG. 4 is a schematic view of the replica eye of FIG. 1 in a first state.

In use, referring to FIG. 4, when the driving member 400 rotates the transmission mechanism 300, centrifugal forces are imparted on the heavy blocks 250. Accordingly, the heavy blocks 250 move away from the rotor 302 in a radial direction along the corresponding spokes 308. The pupil portion 202 and the iris portion 204 of the resilient film 400 are stretched from an original size, thus dilation of the pupil portion 202 occurs. At the same time, the flexible components 230 and the resilient film 200 are stretched and generate restoring forces.

Figure 5:
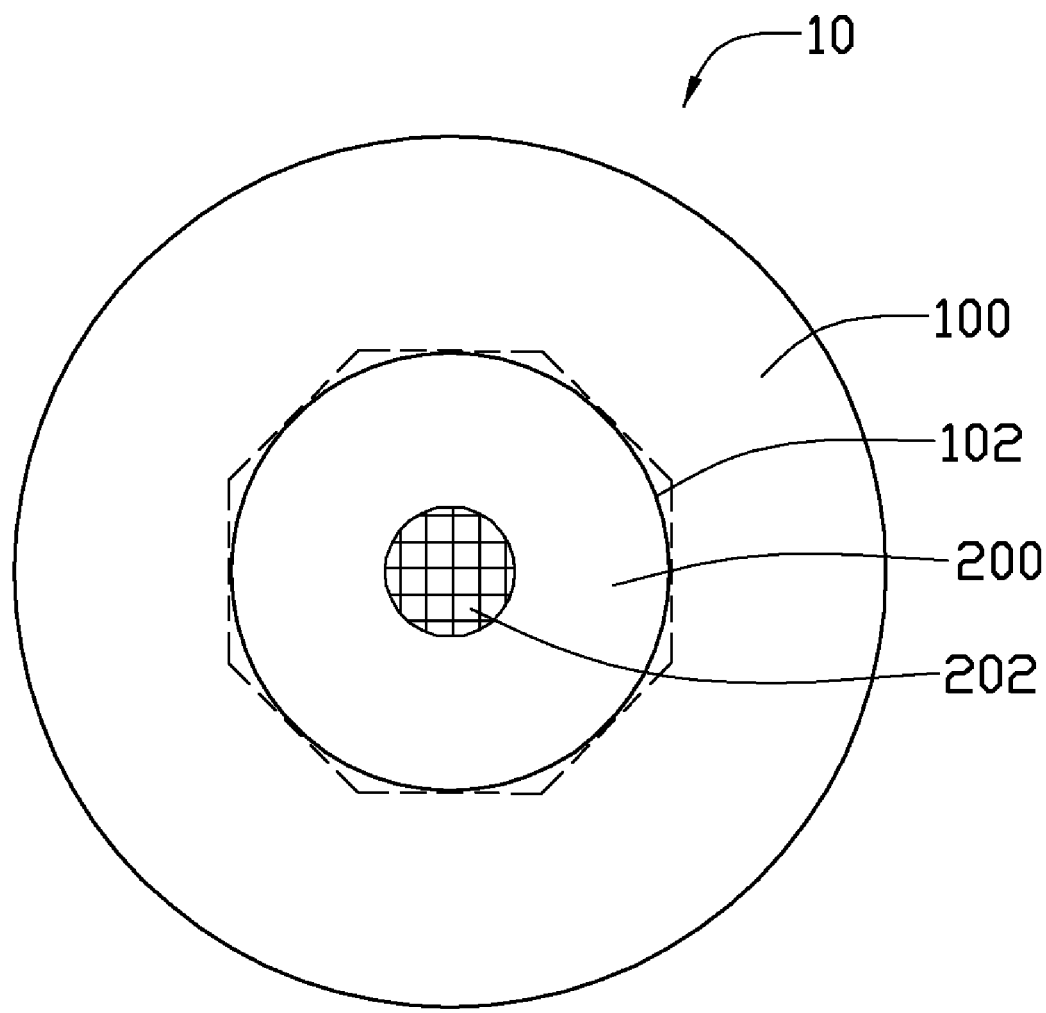
FIG. 5 is a schematic view of the replica eye of FIG. 1 in a second state.

Referring to FIG. 5, when the driving member 400 stop rotating the transmission mechanism 300, the centrifugal forces acting on the heavy blocks 250 are terminated. The flexible components 230 and the resilient film 200 will succumb to the restoring forces and move towards the rotor 302 along the corresponding spoke 308. At the same time, the heavy blocks 250 is driven by the flexible components 230 and the resilient film 200 to move towards the rotor 302 along the corresponding spoke 308. The resilient film 200 will return to its original size. Therefore, contraction of the pupil portion 202 of the resilient film 400 occurs. In this way the replica eye 10 is able to simulate a living eye that dilates or contracts in manner realistically simulating a living eye.

It is to be understood, however, that even though numerous information and advantages of the present embodiments have been set forth in the foregoing description, together with details of the structures and functions of the present embodiments, the disclosure is illustrative only; and that changes may be made in detail, especially in matters of shape, size, and arrangement of parts within the principles of the present embodiments to the full extent indicated by the broad general meaning of the terms in which the appended claims are expressed.

What is claimed is:

1. A replica eye, comprising:
   an eyeball in a semi-spherical shape, the eyeball comprising a light-transmitting area for transmitting light;

a resilient film comprising a pupil portion and an iris portion surrounding the pupil portion, the pupil portion being a first color, the iris portion being a second color other than the first color;
a driving member having a shaft, the driving member providing rotating forces to the shaft; and
a transmission mechanism comprising a rotor fastened on the shaft of the driving member, and a plurality of flexible members in radial arrangement, a first end of each flexible member away from the rotor being fastened on an outer edge of the resilient film;
wherein when the driving member rotates the transmission mechanism, centrifugal forces are imparted on the plurality of flexible members, the plurality of flexible members will move away from the rotor along a radial direction and stretch the pupil portion and the iris portion, thus the pupil portion viewable from the light-transmitting area is expanded, at the same time the plurality of flexible members are stretched to generate restoring forces.

2. The replica eye according to claim 1, wherein when the driving member stops rotating the transmission mechanism, the centrifugal forces acting on the plurality of flexible members are terminated, the plurality of flexible members succumbs the restoring forces to move towards the rotor and contract the pupil portion and the iris portion, thus contraction of the pupil portion viewable from the light-transmitting area is replicated.

3. The replica eye according to claim 1, wherein the transmission mechanism further comprises a plurality of spokes in radial arrangement extending from the rotor, the plurality of fixing members are sleeved on and slidable with respect to the corresponding spokes.

4. The replica eye according to claim 3, wherein the transmission mechanism further comprises an outer wheel, the rotor is arranged in the center of the outer wheel, the spokes terminate in the outer wheel.

5. The replica eye according to claim 3, wherein the transmission mechanism further comprises an inner wheel, the rotor is arranged in the center of the inner wheel, the plurality of spokes pass through the inner wheel, a second end of each flexible member opposite to the first end is connected to the inner wheel.

6. The replica eye according to claim 1, wherein the flexible member comprises a flexible component and a block connected to one end of the flexible component away from the rotor, the block is positioned in the first end and fastened on the outer edge of the resilient film.

7. The replica eye according to claim 1, further comprising a baseboard; the resilient film, the driving member and the transmission mechanism being received in the eyeball, the driving member being fastened on the baseboard.

8. A replica eye, comprising:
an eyeball being semi-spherical;
a resilient film received in the eyeball, the resilient film comprising a pupil portion and an iris pupil portion surrounding the pupil portion, the pupil portion being a first color, the iris portion being a second color other than the first color;
a transmission mechanism comprising a rotor, a plurality of spokes and a plurality of blocks; the plurality of spokes extending from the rotor, the plurality of blocks being sleeved on and slidable with respect to the corresponding spokes, the plurality of blocks being fastened to outside edges of the resilient film; and
a driving member comprising a shaft fastened to the rotor of the transmission mechanism, the driving member being configured to provide rotating force for the shaft.

9. The replica eye according to claim 8, wherein the transmission mechanism further comprises an outer wheel and an inner wheel, the outer wheel and the inner wheel are concentric circles, the plurality of spokes pass through the inner wheel and terminate at the outer wheel, and the block is arranged between the inner wheel and the outer wheel.

10. The replica eye according to claim 9, wherein the transmission mechanism further comprises a plurality of flexible components, each flexible component is connected between the inner wheel and the corresponding block.

11. The replica eye according to claim 9, further comprising a baseboard; the resilient film, the driving member and the transmission mechanism being arranged between the eyeball and the baseboard, the driving member being fastened on the baseboard.

12. A replica eye, comprising:
an eyeball in a semi-spherical shape, the eyeball comprising a light-transmitting area for transmitting light;
a resilient film comprising a pupil portion and an iris portion surrounding the pupil portion, the pupil portion being a first color, the iris portion being a second color other than the first color;
a transmission mechanism connected with an outer edge of the resilient film; and
a driving member configured to rotate the transmission mechanism;
wherein when the driving member rotates the transmission mechanism, the transmission mechanism stretches the resilient film such that an area in combination of the pupil portion and the iris portion is viewable from the light-transmitting portion to be increased, thereby dilation of the replica eye is replicated.

13. The replica eye according to claim 12, wherein when the driving member stops rotating the transmission mechanism, the transmission mechanism contracts the resilient film such that areas of the pupil portion and the iris portion viewable from the light-transmitting portion are contracted, thereby contraction of the replica eye is replicated.

14. The replica eye according to claim 12, wherein the transmission mechanism comprises a plurality of blocks connected to the outer edge of the resilient film, when the driving member rotates the transmission mechanism, centrifugal forces are imparted on the plurality of blocks, the plurality of blocks move and stretch the pupil portion and the iris portion, thereby the resilient film generates restoring forces.

15. The replica eye according to claim 14, wherein when the driving member stops rotating the transmission mechanism, the centrifugal forces acting on the plurality of flexible members are terminated, the resilient film succumbs to the restoring forces and contracts, such that areas of the pupil portion and the iris portion viewable from the light-transmitting portion are contracted, thereby contraction of the replica eye is replicated.

16. The replica eye according to claim 14, wherein the transmission mechanism further comprises a rotor connected with the driving member, a plurality of spokes extending from the rotor, and the blocks sleeved on and slidable with respect to the corresponding spokes.

17. The replica eye according to claim 16, wherein the transmission mechanism further comprises an outer wheel at which the plurality of spokes end, the plurality of blocks are arranged between the outer wheel and the rotor.

18. The replica eye according to claim 17, wherein the transmission mechanism further comprises an inner wheel passed by the spokes and a plurality of flexible components, the plurality of blocks are arranged between the inner wheel and the outer wheel; the flexible components are connected between the inner wheel and the corresponding blocks.

19. The replica eye according to claim 18, wherein the rotor is arranged in the center of the outer wheel, the outer wheel and the inner wheel are concentric circles.

20. The replica eye according to claim 12, further comprising a baseboard; the driving member being fastened on the baseboard, and the driving member, the transmission mechanism and the resilient film being arranged between the eyeball and the baseboard.

* * * * *